United States Patent [19]

Verhoff et al.

[11] Patent Number: 5,833,757
[45] Date of Patent: Nov. 10, 1998

[54] PROCESS FOR CONVERSION OF BANANAS TO SUGAR SYRUP

[75] Inventors: Francis H. Verhoff, Cincinnati, Ohio; Charles S. Blatteis, Cypress, Tex.; Cheryl L. Barrett, Cleveland, Wis.

[73] Assignee: U.S. Tech, Inc., Cincinnati, Ohio

[21] Appl. No.: 577,051

[22] Filed: Dec. 22, 1995

[51] Int. Cl.⁶ .............................. C13D 1/08; C08B 30/00; A23L 1/10; A23B 7/10
[52] U.S. Cl. ................................ 127/42; 127/29; 127/44; 127/65; 426/28; 426/48; 426/49; 426/52; 426/658
[58] Field of Search .................................. 127/29, 42, 44, 127/65; 426/28, 48, 49, 52, 658

[56] References Cited

U.S. PATENT DOCUMENTS

| | | | |
|---|---|---|---|
| Re. 34,237 | 4/1993 | Sole | 426/49 |
| 3,615,721 | 10/1971 | Silberman | 99/199 |
| 3,849,194 | 11/1974 | Armbruster et al. | 127/29 |
| 3,922,196 | 11/1975 | Leach et al. | 127/29 |
| 4,017,363 | 4/1977 | McMullen et al. | 127/29 |
| 4,267,196 | 5/1981 | Johnston | 426/49 |
| 4,282,319 | 8/1981 | Conrad | 435/69 |
| 4,287,304 | 9/1981 | Muller et al. | 127/38 |
| 4,361,651 | 11/1982 | Keim | 435/161 |
| 4,377,602 | 3/1983 | Conrad | 426/656 |
| 4,410,368 | 10/1983 | Takasaki et al. | 127/42 |
| 4,456,714 | 6/1984 | Cox et al. | 524/56 |
| 4,511,654 | 4/1985 | Rohrbach et al. | 127/55 |
| 4,565,702 | 1/1986 | Morley et al. | 426/93 |
| 4,689,088 | 8/1987 | Morehouse et al. | 127/29 |
| 4,857,339 | 8/1989 | Maselli et al. | 426/28 |
| 4,857,356 | 8/1989 | Reinl et al. | 426/620 |
| 4,874,617 | 10/1989 | Sole | 426/49 |
| 4,921,709 | 5/1990 | Sole | 426/49 |
| 4,935,254 | 6/1990 | Nunez | 426/304 |
| 4,959,483 | 9/1990 | Matsumura et al. | 549/315 |
| 4,971,824 | 11/1990 | Jonas | 426/565 |
| 5,411,755 | 5/1995 | Downton et al. | 426/599 |
| 5,422,136 | 6/1995 | Fuisz | 426/658 |
| 5,433,965 | 7/1995 | Fischer et al. | 426/548 |

OTHER PUBLICATIONS

"Preparation of Glucose and High Fructose Syrups from Bananas (Musa Cavendishii)," by P.J. Van Wyk, E.A. Heinen, and L.G.J. Ackermann published in *Lebensmittel Wissenschaft und technologie*, vol. 11, pp. 29–30 (1978) Jul. 1977.

Primary Examiner—Mark L. Bell
Assistant Examiner—Patricia L. Hailey
Attorney, Agent, or Firm—Philip G. Meyers

[57] ABSTRACT

A process which permits the facile conversion of green bananas to a sugar syrup uses a sequence of steps involving grinding the bananas, heating the bananas, treating the bananas with an alpha amylase to convert the starch granules into lower molecular weight molecules (liquefaction), changing conditions and treating the low molecular weight starch molecules and other substances in the liquefied fluid with the enzymes, amyloglucosidase, pectinase, cellulase, macerase, etc., filtering the resultant fluid to remove the solids, and, if necessary, evaporating the sugar solution to a suitable concentration. Use of elevated pH in each of the enzymatic conversion steps was found to greatly increase the glucose yield.

17 Claims, 1 Drawing Sheet

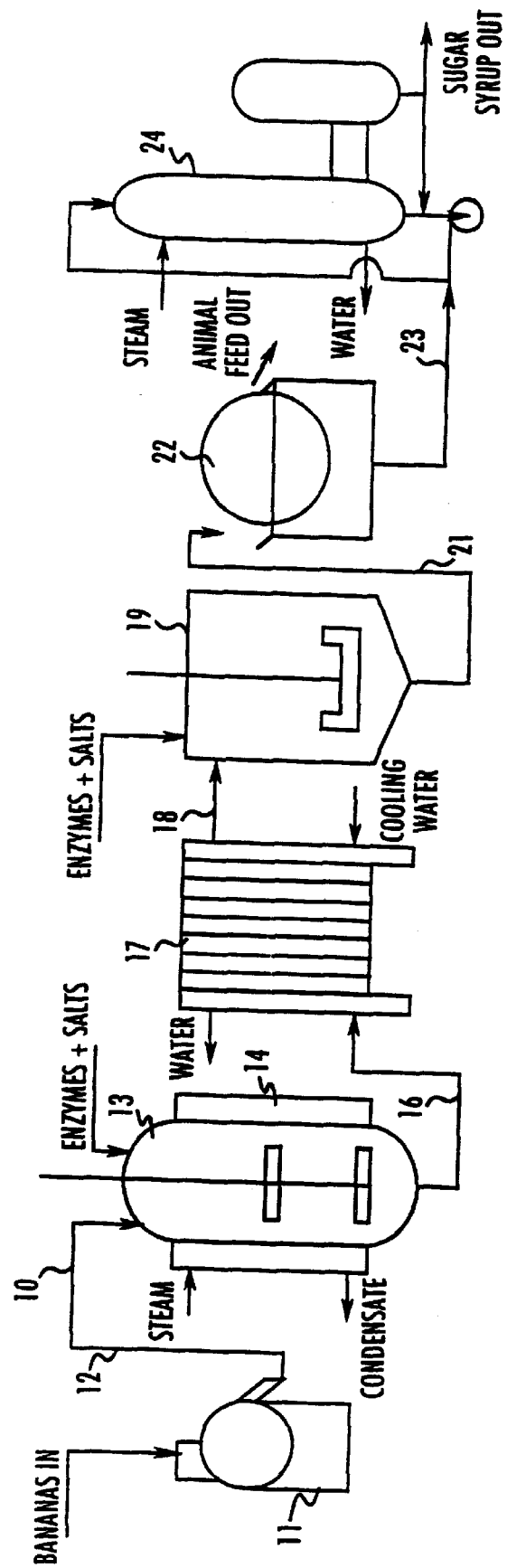

PROCESS FOR CONVERSION OF BANANAS TO SUGAR SYRUP

TECHNICAL FIELD

This invention relates to the conversion of the starch and other carbohydrates in bananas to a sugary syrup using an enzyme-based process.

BACKGROUND OF THE INVENTION

Sugars have been produced from agricultural products for centuries primarily for use as nutritive sweeteners for foods. However, sugars have other uses as fermentation substrates for the production of various products, including antibiotics, citric acid, and others. The main source of nutritive sweeteners for several hundred years has been the sugar beet and sugar cane. The beets and cane naturally produce sucrose, and this sucrose is recovered from the plants in a sugar factory. This sugar is recovered as a solid (e.g., table sugar) or as a liquid (sugar syrup).

Within the last twenty years, the production of a sweet sugar syrup from starch has developed into a large industry. The ready availability of corn at low prices was an incentive to consider it as a raw material for the production of sugar syrup. The primary technological development which permitted this development was the production of inexpensive enzymes for the conversion, namely alpha amylase, amyloglucosidase, and the glucose isomerase. The high fructose corn syrups which developed from this technology now account for about one-third of the sugar market in the United States.

Most high fructose corn syrups are made by a wet milling process, though a dry milling process is also sometimes used. In the wet milling process, the corn is steeped in water containing sulfur dioxide. After steeping, the corn is coarsely ground in water and the germ removed (oil and gluten are made from the germ). The remaining slurry primarily containing starch and fiber is ground to fine particles in water. The fiber is then filtered from the starch slurry. The starch slurry is then converted to glucose- and fructose-containing syrups using the above-described enzymes.

As the market for the high fructose corn syrups developed, considerable research was directed towards reducing the cost of the enzymes, understanding their properties, and optimizing their utility in converting starch to glucose. Thus, information is now available on the proper use of these enzymes especially concerning optimum temperature, pH, solids concentration, and the like.

The key steps in the conversion of corn starch to sugar syrup are the treatments with the enzymes, alpha amylase and amyloglucosidase. The conversion of starch granules to a liquid slurry which contains starch molecules of shorter length is normally referred to as starch liquefaction. This process uses the enzyme alpha amylase which attacks the starch molecule at random locations, producing new starch molecules of shorter length and reducing the length of the starch molecules. Heat is important in this process to accelerate the starch dissolution process and decrease the viscosity of the slurry.

Generally, it is accepted that temperatures above 100° C. are needed for this process, and sometimes temperatures up to 150° C. are used. It is also well known that a lower (acidic) pH helps in the liquefaction of starches. In fact, one old process for producing sugar syrups involved using low pH conditions to convert the starch to sugar syrups. In such an enzymatic process, the pH and temperature of the process are determined by the conditions suitable for use of the enzyme. For the typical commercial thermal stable bacterial alpha amylase enzyme, the optimal temperature range is 90° C. to 95° C. and the optimal pH range from 5.5 to 7.0. Thus, the known practice for the liquefaction of starch is to apply a relatively high temperature and a lower pH.

The second enzymatic process is the conversion of the liquefied starch to a sugar syrup (saccharification). The primary enzyme used for this conversion is a fungal amyloglucosidase (also known as glucoamylase). This enzyme attacks the starch molecules at one end and splits off one glucose molecule at a time. Thus, this enzyme is capable of producing a glucose syrup from the short starch molecules. The optimal pH range for the commercially available glucoamylase is 4.0 to 4.4 and the optimal temperature range is 58° C. to 65° C. Therefore, the temperature and pH have to be changed between the treatment with alpha amylase and glucoamylase.

Other enzymes have been used in unit operations to reduce viscosity and to convert some of the other carbohydrates present to sugar. For example, in wheat conversions, beta glucosidase is sometimes used. However, there have not been significant published studies on the use of other enzymes in saccharification. In commercial practice, other enzymes have not been found useful in saccharification and therefore, none are typically used.

Many agricultural products contain significant quantities of starch, e.g., corn, wheat, rice, potatoes, cassava, sweet potatoes, and other grains and tubers. Bananas contain a significant amount of carbohydrate as starch and sugars. On a dry basis, this carbohydrate content can vary from about 75% to 90% depending upon the variety and growing conditions of the bananas. In green bananas, the carbohydrate is almost exclusively as starch. As the banana ripens, the native enzymes in the banana convert the starch to sugar, giving the ripe banana its sweet flavor. This ripening requires holding the bananas under controlled conditions for a week or more. For the production of bananas for retail sale in a grocery store, the bananas are picked green (only those of the correct size and complexion are picked), sorted according to appearance, ripened in containers, and shipped to market.

Because the fresh banana market requires only bananas of the correct size and appearance, many bananas are not deemed suitable for market and are left in the plantations or culled from those prepared for shipment. It is estimated that only half or less of the bananas produced in the plantations are shipped to market. Therefore, a significant portion of the bananas are left at the plantation or packing plant. These bananas presently go to waste or are used as animal feed.

These waste bananas are green bananas and therefore contain significant amounts of starch. Green bananas could thus be used as a source of starch for the production of sugar syrups in an enzymatic process as done with other sources of starch. The sugar syrups thus produced could be used in the production of various fermentation products such as antibiotics, amino acids, and organic acids such as citric acid.

There has been one study on the conversion of bananas to sugar syrups "Preparation of Glucose and High Fructose Syrups from Bananas (Musa Cavendishii)," by P. J. Van Wyk, E. A. Heinen, and L. G. J. Ackermann published in *Lebensmittel Wissenschaft und Technologie*, vol 11, p. 29–30 (1978). In this paper, bananas of various stages of ripeness were considered. The one green banana study by Van Wyk et al. generated a starch conversion of about 49%, too low for commercial practice. The present invention seeks to provide an enzymatic process that can produce a high quality sugar end product with high efficiency.

SUMMARY OF THE INVENTION

The process of the present invention permits the facile conversion of green bananas to a sugar syrup. Such a process includes the basic steps of (a) grinding bananas to form a fine solids;

(b) then liquefying the solids by treatment of the solids with an alpha amylase enzyme effective to reduce the length of starch molecules present in the solids; and (c) then saccharifying starch in the liquefied solids to sugar by treatment of the liquefied solids with an amyloglucosidase enzyme.

According to one aspect of the invention, it has been discovered that conducting the first enzyme conversion step (b) at a basic pH in a manner contrary to accepted practice for other agricultural products such as corn greatly increases the speed of the reaction and the glucose yield. A further improvement was obtained when the second enzyme conversion step (c) was conducted at a higher pH than the range recommended for the amyloglucosidase enzyme. According to another aspect of the invention, the first enzyme conversion step (b) is preceded by treating the solids with a macerating enzyme under conditions effective to break down polysaccharides and soften the solids. This again is contrary to conventional practice with other common sources of starch, wherein a macerating enzyme is not used in this manner. When one or more of the foregoing measures are used in accordance with the invention, it has been found that the glucose yield of the syrup product can be greatly increased and the speed and efficiency of the conversion process much improved.

The invention further provides an apparatus for carrying out the foregoing process, along with a concentrated sugar syrup made from bananas having a glucose content of at least about 55 wt. %, and a byproduct composition useful as an animal feed that is removed from the sugar syrup during filtration. These and other aspects of the invention are set forth in the detailed description which follows.

BRIEF DESCRIPTION OF THE DRAWING

The drawing is a schematic diagram of an apparatus for carrying out the process of the invention.

DETAILED DESCRIPTION

Green bananas which are obtained from the banana plantations or are culled from the packaging plant are used in this process. The bananas are handled by the process of the invention within a few days after picking. A preferred embodiment of the process of the invention uses a sequence of unit operations involving grinding the bananas, heating the bananas, treating the bananas with an alpha amylase to convert the starch granules into lower molecular weight molecules (liquefaction), treating the low molecular weight starch molecules and other substances in the liquefied fluid with the enzymes amyloglucosidase, pectinase, cellulase, macerase, and optionally others selected for carbohydrates naturally present in bananas in significant quantities, optionally filtering the resultant fluid to remove the solids, and, if necessary, evaporating the sugar solution to a suitable concentration. For purposes of the invention, the sugar produced is primarily glucose, but other types of sugars may also be present in the syrup product. It has been discovered according to the invention that using certain conditions for these steps, particularly controlling pH during the enzymatic conversions, has a dramatic effect on the overall effectiveness of the process as will be shown in the examples which follow.

The drawing illustrates an apparatus 10 for carrying out the unit operations involved in the conversion of green bananas to a sugar syrup according to the invention. The operations shown in the figure include the grinding of the bananas in a grinder 11, the liquefaction of the starch in a reactor 13, the cooling of the liquefied slurry in a heat exchanger 17, the saccharification of the starch and the conversion of other carbohydrates in the slurry to sugars in a second reactor 19, the filtration of the solids from the resulting slurry in a filtration device 22, and the evaporation of the sugar solution to a higher concentration if necessary in an evaporator 24. It is also possible to treat this sugar solution with further unit operations such as ion exchange, or carbon treatment to produce a sugar syrup with fewer impurities.

The first unit operation is the grinding of the bananas, preferably to a paste consistency. This can be accomplished in a number of ways including the direct grinding of the hard green bananas in the grinder 11. It is possible to add water to the bananas to facilitate the grinding of the bananas. Further, cooking the bananas before grinding can make grinding the bananas easier. Such a cooking step, if used, involves heating the bananas to a temperature in the range from about 50° C. to 100° C. for at least about 10 minutes, preferably from 10 to 60 minutes, to soften the bananas without excessively degrading them. The bananas may be sliced prior to cooking. A cooking tank (not shown) may be provided upstream from grinder 11 to carry out the cooking step.

The output of grinder 11 should be a solid which is finely ground, a solid of a paste consistency, or a slurry of fine ground solids. These solids are transferred through a line 12 to the liquefaction reactor 13, preferably a stirred pressure vessel with steam jacket or coils 14 for heating. Sufficient water is added into reactor 13 to make a stirable paste or slurry of the banana solids. In some instances, it is not necessary to add water. Any salts which are needed for the enzymes are also added into reactor 13, e.g., a calcium salt to provide calcium ions required for the thermal stable alpha amylase. The alpha amylase used in the process of the invention is derived from fungal, bacterial or other known sources. The natural amylytic enzymes of the bananas do not convert nearly enough starch to sugar for purposes of the invention, and thus it is necessary to add the alpha amylase.

The slurry is heated by steam jacket or coils 14 to help break down the starch granules and molecules. The maximum temperature achieved in this heating is preferably in the range of about 65° C. to 150° C., more generally 80° C. to 150° C. However, to the extent that a temperature of from 65°–100° C. or 80°–100° C. can be used, energy is conserved and reactor 13 may be a simple stirred tank instead of a pressure vessel.

The pH is adjusted to a level suitable for the enzyme used in this reactor. While a wide pH range including acidic pH's as low as 5.0 may be employed with some degree of success as shown in the examples below, a neutral or most preferably a basic pH in the range of 7.0 to 9.0, especially 7.5 to 8.5, is most preferred for the treatment with the alpha amylase enzyme. The enzyme and salts may be added before or after heating commences. Various alpha amylases may be used, but a thermal stable bacterial alpha amylase is preferred.

The temperature of the slurry does not need to remain constant. For example, the banana slurry could first be heated to 120° C. and then cooled down to 90° C., at which time the enzymes and salts are added. Such a temperature decrease has been conventionally used for corn and other suitable plants, and may be used in the process of the present invention as well. The slurry is maintained at the final temperature after the enzyme is added for a period of longer than 5 minutes. The completion of the reaction is determined as the time that the slurry becomes starch negative according to an iodine test.

Prior to the liquefaction, the mixture may be treated with a macerating enzyme to permit more complete liquefaction of the starch. The conditions in the reactor are adjusted to be optimal for this enzyme, namely a temperature of from 20° C. to 60° C. and a pH in the range of 3.5 to 6.5. For purposes of the invention, a macerating enzyme refers to one or a mixture of enzymes that break down carbohydrates present in bananas other than starch, such as pectin, cellulose and the like. The macerating enzyme may break down starch to some extent as well. The improvement in the subsequent liquefaction step appears to result from the softer condition of the banana solids due to partial breakdown of solids present not affected by the alpha amylase.

After the slurry is starch negative, the liquefaction is complete. The slurry is discharged from reactor 13 and fed through a line 16 to a heat exchanger 17 wherein the treated banana material is cooled to between about 30° C. and 70° C., generally 40° C. to 70° C. The cooled material is then fed through a line 18 to a second saccharification reactor 19, which may be a stirred steel tank.

In the second reactor 19, the pH is adjusted to between 3.5 and 7 for the saccharification reaction. Although more acidic pH levels will work, an unexpected increase in glucose yield is observed when a pH in the range from 5.5 to 7 is used. The pH is usually adjusted down by addition of a mineral acid such as hydrochloric acid or sulfuric acid, but it is possible to use an organic acid such as acetic acid or citric acid. Sometimes it is necessary to add water to dilute the mixture to a desired solids content.

The fungal glucoamylase is added to the enzyme mixture in reactor 19 to convert the starch molecules to glucose. In order to convert some of the other materials occurring naturally in bananas to sugars and to reduce the viscosity of the mixture, it is preferable to add a mixture of macerase enzymes including pectinase, cellulase, hemicellulase, arabanase, polygalacturonase, and other enzymes. Pectinases are important because bananas are known to contain substantial amounts of pectin, but using a mixture of two, preferably three or more enzymes providing the foregoing enzyme activities is most preferred. The mixture in reactor 19 is allowed to react for at least 4 hours, preferably between 8 and 48 hours, at the desired temperature.

After the saccharification reaction is complete, the slurry is fed through a line 21 to be filtered in a filtration device 22, such as a rotary vacuum filter. A filter aid may be used if necessary. Wash water may be applied to the filter cake to reduce the loss of sugar syrups in the cake. Other types of solids separators including pressure leaf filters, plate and frame filters, Funda types of filters, and centrifuges could also be used.

After the filtration is complete, the saccharified product may if necessary be fed through a line 23 to an evaporator 24 to evaporate some of the water from the solution coming from the filter device 22. This resulting solution might be satisfactory for various uses. If, however, a more pure sugar syrup is required, the syrup could be treated with an ion exchange resin (both cation and anion as necessary) and with carbon absorption.

The foregoing process can convert green bananas into a sugar syrup suitable for use in foods or as a substrate for fermentation to make antibiotics, amino acids, and organic acids such as citric acid. The sugar syrup after filtration and concentration preferably contains 55 to 85 wt. % dissolved glucose and the balance essentially water with substantially no solid particulates. The foregoing range provides a sufficiently high glucose concentration without rendering the syrup too thick. The exact composition of this syrup derived from bananas is unique and chemically different from glucose syrups of similar concentration derived from starch sources other than bananas.

The byproduct of the process, namely the solids removed by the filtration device 22, have a high protein content (at least 10 wt. % of the solids, generally 10–20 wt. %) and can be advantageously used as an animal feed. An analysis of a sample of this material indicated 25.5 wt. % total solids. The solids consisted of 16.1 wt. % protein and 5.9 wt. % fat, the balance being fiber, carbohydrates, ash and other solids.

The invention will be further described by reference to the following examples and comparative examples.

COMPARATIVE EXAMPLE 1

Bananas were purchased as green as possible in a grocery store. One batch of approximately 500 grams of whole bananas (peel and pulp) was ground in a Waring blender, and enough water was added to make it capable of being stirred. This mixture was treated with fungal alpha amylase (Clarase from Solvay Enzymes) at 60° C. and a pH of 5.0 based upon the recommendation of the enzyme manufacturer. The resultant mixture was starch positive according to an iodine test, signifying incomplete starch conversion, and was not suitable for further testing.

COMPARATIVE EXAMPLE 2

A further batch of approximately 500 grams of bananas was ground in a Waring blender and water was added as needed to reduce the viscosity. This mixture was heated to 121° C. for 15 minutes. The mixture was then treated with a thermal stable bacterial alpha amylase (Takatherm L-340 from Solvay Enzymes, referred to as Takatherm hereafter) at 95° C. and a pH of 6.5 as recommended by the enzyme manufacturer. The resulting mixture tested starch positive and was not treated further. Comparative Examples 1 and 2 show that the known methods for converting starch to sugar syrups for other common sources of starch would not be successful with bananas.

EXAMPLE 1

Approximately 500 grams of whole green bananas from the grocery store were ground in a Waring blender and sufficient water added to make a flowable banana slurry. This banana slurry was treated with a mixture of macerase enzymes (Macerex, a macerating enzyme from Solvay Enzymes, a combination of various enzymes including pectinase, arabanase, cellulase, hemicellulase, etc.) at 50° C. and a pH of 5.0 for 1 hour. This mixture was then treated with a thermal stable alpha amylase (Takatherm) at 95° C. and a pH of 6.5. After one hour of treatment it tested starch negative. The mixture was then treated at 50° C. and pH of 4.5 with a fungal glucoamylase (Diazyme L-200 from Solvay Enzymes). The resulting mixture indicated a 67% conversion of the total solids to sugars. The pretreatment with a macerase enzyme enhanced the glucose yield and made it possible to reach a starch negative endpoint in the first enzymatic conversion step.

EXAMPLE 2

Again approximately 500 grams of green bananas obtained from the local grocery store were ground in a Waring blender and sufficient water added to reduce the viscosity. This mixture was subjected to the same treatment with the macerase enzyme as in Example 1. It was then treated with a fungal alpha amylase (Clarase) at 60° C. and pH of 5.0. The resulting mixture was then treated with a fungal glucoamylase (Diazyme L-200) at a pH of 4.5 and 50° C. The resulting mixture indicated a conversion of 69% of the solids to sugars.

EXAMPLE 3

In order to test the process of Example 2 on genuine green bananas from plantations, green bananas were shipped via air freight from Ecuador in 2 days. These bananas were tested in the conversion procedures using only the thermal stable bacterial alpha amylase. These bananas proved to be too hard to be directly ground in the Waring blender. Therefore, the bananas were cut into pieces of approximately one half an inch in length and boiled in approximately the same amount of water for one hour. After this treatment the bananas could be ground in the Waring blender.

Whole green bananas of the Bonita type obtained from Ecuador as indicated above were cut into pieces and boiled for one hour. The bananas were homogenized in a laboratory Waring blender with only enough water added to achieve good blending. The mash thus formed was treated with 0.09 ml of Macerex at 50° C. for one hour. The slurry was then adjusted to pH 6.5 and calcium ion was added as calcium chloride to 100 ppm. Thermal stable bacterial alpha amylase (Takatherm) was added at 0.25 ml per kilogram of dry solids. The mash (slurry) was heated to 121° C. for 15 minutes and then cooled to 95° C. After equilibration to 95° C., an additional 0.5 ml Takatherm per kg of dry solids was added to the mash. The mash was held at 95° C. until the iodine test was starch negative.

The mash was then cooled to 60° C. and adjusted to a pH of 4.5 with sulfuric acid. Fungal glucoamylase (Diazyme L-200) was added at the rate of 200 dextrose units (DU) per gram of dry solids. This material was held at temperature for 72 hours with samples taken every 24 hours. The final mash was filtered easily on a Buchner funnel. The final filtered product contained almost exclusively the sugar glucose. The dry solids content of this liquid was about 8.1% and the glucose content was 67.2% of the dry solids.

EXAMPLE 4

Another sample of the Bonita bananas which had been kept in cold storage for a longer period of time (about 14 days) was subjected to the same procedure as described in Example 3. The final product contained a dry solids content of 9.9% and a glucose 68% of the dry solids.

EXAMPLE 5

A sample of HB type bananas was subjected to the same procedure as described in Example 3. After completion of the process, the filtered product had a dry solids content of 10.8% and the glucose content was about 69% of the dry solids.

EXAMPLE 6

A second sample of HB type bananas which had been stored for a longer period of time than those in Example 5 was subjected to the same procedure as described in Example 4. After completion of the process, the dry solids content of the filtered product was 11.5% and the glucose content was 70.8% of the dry solids.

EXAMPLE 7

The procedure as detailed in Example 3 was performed on bananas except that no water of dilution was added to the mash produced in the Waring blender. The treatment with the Takatherm did not yield a mash that was starch negative with the iodine test. However, the experiment was continued with the treatment using Diazyme. The resulting product after filtration had a solids content of 18% and a glucose content of 71%.

Further work was done on the liquefaction step to determine if higher temperatures than 121° C. would be beneficial for the conversion of the starch to a starch negative result with the iodine test. Increased temperature did not appear to help the conversion as expected. However, in one experiment the pH was raised outside the normal range used for the Takatherm enzyme. Surprisingly, the liquefaction process rapidly produced a starch negative result without the temperature being raised to the high levels previously attempted. The following examples will illustrate these results with first an experiment at a lower pH which is known to help hydrolyze starch, followed by the experiments at higher pH.

COMPARATIVE EXAMPLE 3

Green Bonita bananas (488 grams) were sliced and boiled in 500 ml of water. Much of the water was boiled off before the bananas were ground in the Waring blender. To this mixture was added 500 ml water, 1 ml Takatherm, and 1.0 g $CaCl_2$. This mixture was boiled at 100° C. for two hours at pH 5.3. The mixture was starch positive by the iodine test. Another 1 ml of Takatherm was added, and the mixture was boiled for another hour at 100° C. The mixture was still starch positive. This mixture was then autoclaved at 121° C. for 30 minutes and returned to 95° C. and another 1 ml of Takatherm was added and mixed for 1.5 hours. The resultant mixture was still starch positive.

Another experiment was performed at a pH of 5.3 using a mixture of different enzymes as pretreatments (Clarase, Clarex, Macerex, Diazyme) to hopefully convert the starch. No pretreatments were successful since all treatments at this pH ended in starch positive mixtures.

EXAMPLE 8

Green Bonita bananas (470 grams) were sliced into 470 ml of water and blended. This mixture was autoclaved for 30 minutes at 121° C. and transferred to a vessel at 95° C. To this mixture was added 1 g $CaCl_2$ and 1 ml Takatherm. After two hours this mixture was starch positive. Then 2.0 ml 10N KOH was added and the pH raised to 8.5. One more ml of Takatherm was added. The mixture was almost immediately starch negative. The iodine test was able to detect starch up to pH of 9.5.

This result of this example was surprising because it was not expected that such a high, basic pH would give good results. Further experiments were therefore performed using a higher pH for the first enzymatic conversion.

EXAMPLE 9

One kilogram of sliced bananas were put in one liter of water and boiled for thirty minutes, then blended in the Waring blender. The pH was adjusted to 7.8 with 3.5 ml. of 10N KOH and the material was divided into two parts. To the first half, 1.0 ml of Takatherm and 1.0 gram of CaCl$_2$ were added, and the material was autoclaved for 30 minutes at 121° C. The material was then transferred to a vessel at 95° C. and another 1.0 ml of Takatherm was added. After 30 minutes, the mixture became starch negative. To the second half, 0.5 ml of Takatherm and 0.5 g of CaCl$_2$ were added. The temperature was raised to 95° C. for 30 minutes, and the mixture became starch negative according to the iodine starch test.

The second half of the mixture was reduced in temperature to 50° C. and the pH lowered to 5.0. This mixture was then divided into two parts of 400 ml of mash. To one of these 400 ml samples was added 0.5 ml Diazyme, 0.25 ml. of Clarex, Cellulase, and Macerex. This mixture yielded a clarified solution of 14.5% solids and 79.7% glucose on a dry solids basis. The second 400 ml sample was treated with 0.25 ml of Diazyme and of Clarex and 0.5 ml of Cellulase and Macerex. The resulting sugar syrup product contained 14.7% dry solids and 78.6% glucose on a dry solids basis. The improvement in glucose yield can be directly attributed to the use of a higher pH in the amylase conversion step.

EXAMPLE 10

Nine hundred grams of green bananas were boiled in 900 ml of water for 30 minutes. The mixture was then ground in a Waring blender and adjusted to a pH of 7.7 with 3 ml of 10N KOH. This mixture was brought to 95° C., 2.0 ml of Takatherm and 2.0 grams of CaCl$_2$ were added to the mixture, and it was held for 15 minutes when it became starch negative. The mixture was then cooled to 60° C., adjusted to a pH of 5.0 and divided into four different portions of 400 ml each. To the first portion was added 0.5 ml of each of the following enzymes: Diazyme, Clarex, Cellulase, and Macerex (all Solvay Enzymes). The resulting sugar syrup product had 18.0% dry solids and 75.9% glucose on a dry solids basis. To the second portion of the mixture was added 0.5 ml of Diazyme and Clarex and 1.0 ml of Cellulase and Macerex. The resulting sugar syrup product had 18.3% dry solids and 78.8% glucose on a dry solids basis. To the third portion of the mixture was added 0.5 ml of Diazyme and 1.0 Pectinex Ultra SP (Novo Nordisk Enzymes). The resulting sugar syrup product had 18.3% dry solids and 79.5% glucose on a dry solids basis. To the fourth portion of the mixture was added 0.5 ml of Diazyme and 1.0 ml of PMLX (Valley Research). The resulting sugar syrup product had 18.0% dry solids and 78.3% glucose on a dry solids basis. This example shows that a variety of combinations of macerating and starch converting enzymes used in the second stage conversion yielded similar results and did not change the superior yield obtained by using basic pH in the first conversion step.

EXAMPLE 11

To 450 ml of water was added 442 grams of sliced bananas, and the mixture was boiled for 30 minutes. This mixture was then blended and transferred to a 95° C. bath where the pH was adjusted to 7.8 with 2.5 ml of 10N KOH. Two ml of Takatherm and 2.0 grams of CaCl$_2$ was added. This mixture was starch negative after 10 minutes. This material was then cooled to 50° C. and adjusted to a pH of 6.5. The mixture was then divided into two 400 ml portions. To the first portion was added 0.5 ml of the following enzymes: Diazyme, Clarex, Macerex, and Cellulase. The resulting syrup contained 13.3% solids and 84.2% glucose on a dry solids basis. The second portion was treated with 0.5 ml of Diazyme and Pectinex Ultra. The resulting sugar syrup contained 13.3% solids and 84.4% glucose on a dry solids basis. In this example, the combined effects of using elevated pH in both the first and second stage conversions yield a further unexpected increase in overall glucose yield.

The results of the examples and comparative examples are summarized in the table which follows. In the table, percent solids refers to total dissolved solids, a higher percentage representing a higher concentration of solids and a better result. Particulate (undissolved) solids are removed substantially completely by filtration.

TABLE 1

Summary of Examples

| Example: | Amylase Conversion: pH | Amylase Conversion: T° C. | Amylglucosidase Conversion: pH | Amylglucosidase Conversion: T° C. | Preamylase Macerase Treatment? | Starch Negative? | Glucose %/solids % |
|---|---|---|---|---|---|---|---|
| Comp. 1 | 5.0 | 60 | — | — | No | No | — |
| Comp. 2 | 6.5 | 95 | — | — | No | No | — |
| 1 | 6.5 | 95 | 4.5 | 50 | Yes | Yes | 67 |
| 2 | 5.0 | 60 | 4.5 | 50 | Yes | Yes | 67 |
| 3 | 6.5 | 121–95 | 4.5 | 60 | Yes | Yes | 67.2/8.1 |
| 4 | 6.5 | 121–95 | 4.5 | 60 | Yes | Yes | 68/9.9 |
| 5 | 6.5 | 121–95 | 4.5 | 60 | Yes | Yes | 69/10.8 |
| 6 | 6.5 | 121–95 | 4.5 | 60 | Yes | Yes | 70.8/11.5 |
| 7 | 6.5 | 121–95 | 4.5 | 60 | Yes | No | 71/18 |
| Comp. 3 | 5.3 | 100–121 | — | — | No | No | — |
| 8 | 8.5 | 95 | — | — | No | Yes | — |
| 9A | 7.8 | 121–95 | — | — | No | Yes | — |
| 9B-1 | 7.8 | 95 | 5.0 | 50 | No | Yes | 79.7/14.5 |
| 9B-2 | 7.8 | 95 | 5.0 | 50 | No | Yes | 78.6/14.7 |
| 10A | 7.7 | 95 | 5.0 | 60 | NO | Yes | 75.9/18.0 |

TABLE 1-continued

Summary of Examples

| Example: | Amylase Conversion: pH | Amylase Conversion: T° C. | Amylglucosidase Conversion: pH | Amylglucosidase Conversion: T° C. | Preamylase Macerase Treatment? | Starch Negative? | Glucose %/solids % |
|---|---|---|---|---|---|---|---|
| 10B | 7.7 | 95 | 5.0 | 60 | No | Yes | 78.8/18.3 |
| 10C | 7.7 | 95 | 5.0 | 60 | No | Yes | 79.5/18.3 |
| 10D | 7.7 | 95 | 5.0 | 60 | No | Yes | 78.3/18.0 |
| 11A | 7.8 | 95 | 6.5 | 50 | No | Yes | 84.2/13.3 |
| 11B | 7.8 | 95 | 6.5 | 50 | No | Yes | 84.4/13.2 |

The examples as summarized in the preceding table illustrate three unexpected results. First, macerase treatment prior to the normal liquefaction definitely improved the process, in contrast to the result obtained in starch liquefactions of corn and other commercial starch sources. Second, a higher pH is beneficial for the liquefaction, reduces the temperature requirement and speeds the onset of complete conversion (starch negative.) This was not expected because lower pH is known to enhance liquefaction. Third, higher pH also improves the saccharification process. This is totally unexpected because the activity of Diazyme is known to decrease rapidly with higher pH.

The macerating enzymes used in combination with the amylglucosidase also have the important effect of reducing the viscosity of the resulting syrup, rendering it more flowable and easier to handle. In particular, the Pectinex Ultra, Pectinex 100 L, and Viscozyme products were effective to decrease syrup viscosity to 2000–3000 cps, as compared to about 6500 cps for a comparative sample treated with the amylglucosidase only.

It will be understood that the foregoing description is of preferred exemplary embodiments of the invention, and that the invention is not limited to the specific forms shown. For example, although the process has been described for green bananas, it may also be applied to ripened or partially ripened bananas. Further enzyme treatments, such as using a beta amylase to produce maltose, may be used to make sugars other than glucose. These and other modifications may be made in the design and arrangement of the elements without departing from the scope of the invention as expressed in the appended claims.

We claim:

1. A process for the preparation of sugar from bananas, comprising the steps of:
   (a) grinding bananas under conditions effective to form fine banana solids;
   (b) then liquefying the banana solids at a basic pH by treatment of the solids with an alpha amylase enzyme effective to reduce the length of starch molecules present in the solids; and
   (c) then converting starch in the liquefied solids to sugar by treatment of the liquefied solids with an amyloglucosidase enzyme.

2. The process of claim 1, wherein the bananas are green bananas, and further comprising a step of adding water to the banana solids in step (a) or (b) so that the solids are in slurry form in step (b).

3. The process of claim 1, wherein the bananas are green bananas, further comprising cooking the bananas under conditions effective to soften the bananas prior to grinding in step (a).

4. The process of claim 1, wherein step (c) further comprises adding a mixture of macerating enzymes to the solids to convert non-starch carbohydrates to sugar.

5. The process of claim 1, wherein step (b) is carried out at a pH in the range of about 7 to 9.

6. The process of claim 5, wherein step (c) is carried out at a temperature in the range of about 30° C. and 70° C. and a pH in the range of about 5.5 to 7, and step (c) further comprises adding a mixture of macerating enzymes to the solids in amounts effective to convert non-starch/carbohydrates to sugar and reduce the viscosity of the resulting syrup.

7. The process of claim 5, wherein step (b) is carried out at a temperature in the range of about 65° C. to 150° C.

8. The process of claim 5, wherein step (b) is carried out at a pH in the range of about 7.5 to 8.5.

9. The process of claim 1, wherein step (c) is carried out at a pH in the range of about 3.5 to 7.

10. The process of claim 9, further comprising, after step (a) and prior to step (b), treating the solids with a macerating enzyme under conditions effective to break down polysaccharides and soften the solids.

11. The process of claim 9, wherein step (c) is carried out at a temperature in the range of about 30° C. to 70° C.

12. The process of claim 1, further comprising, after step (a) and prior to step (b), treating the solids with a macerating enzyme under conditions effective to break down polysaccharides and soften the solids.

13. A process for the preparation of sugar from bananas, comprising the steps of:
   (a) grinding bananas to form fine banana solids;
   (b) then treating the solids with a macerating enzyme under conditions effective to break down polysaccharides and soften the solids;
   (c) then liquefying the solids by treatment of the solids with an amylase enzyme effective to reduce the length of starch molecules present in the solids; and
   (d) converting starch in the liquefied solids to sugar by treatment of the liquefied solids with an amylglucosidase enzyme.

14. A process for the preparation of sugar from bananas, comprising the steps of:
   (a) grinding bananas under conditions effective to form fine banana solids;
   (b) then liquefying the banana solids by treatment of the solids with an alpha amylase enzyme effective to reduce the length of starch molecules present in the solids; and (c) then converting starch in the liquefied solids to sugar by treatment of the liquefied solids with an amyloglucosidase enzyme and a mixture of macerating enzymes to the solids to convert non-starch carbohydrates to sugar, wherein the treatment with the amyloglucosidase enzyme is carried out at a temperature in the range of about 30° C. and 70° C. and a pH in the range of about 5.5 to 7.

15. A process for producing a solid protein-containing composition from bananas, comprising:

(a) grinding bananas under conditions effective to form fine banana solids;

(b) then liquefying the banana solids by treatment of the solids with an alpha amylase enzyme effective to reduce the length of starch molecules present in the solids; and (c) then converting starch in the liquefied solids to sugar by treatment of the liquefied solids with an amyloglucosidase enzyme to obtain a sugar syrup; and (d) then filtering the sugar syrup to isolate filtered solids therefrom which comprise the solid protein-containing composition.

16. The process of claim 15, wherein step (b) is carried out at a temperature in the range of about 65° C. to 150° C. and a basic pH in the range of about 7 to 9, and step (c) is carried out at a temperature in the range of about 30° C. to 70° C. and a pH in the range of about 3.5 to 7.

17. The process of claim 15, further comprising a step (e) of feeding the solid protein-containing composition to animals.

* * * * *